(12) United States Patent
Zenoni et al.

(10) Patent No.: US 7,560,545 B2
(45) Date of Patent: Jul. 14, 2009

(54) PROCESS FOR OBTAINING CEFOTETAN WITH HIGH YIELD

(75) Inventors: Maurizio Zenoni, Paullo (IT); Antonio Manca, Milan (IT); Riccardo Monguzzi, Dorio (IT)

(73) Assignee: ACS Dobfar S.p.A., Tribiano (IT)

( * ) Notice: Subject to any disclaimer, the term of this patent is extended or adjusted under 35 U.S.C. 154(b) by 543 days.

(21) Appl. No.: 11/383,075

(22) Filed: May 12, 2006

(65) Prior Publication Data

US 2006/0281916 A1 Dec. 14, 2006

(30) Foreign Application Priority Data

Jun. 14, 2005 (IT) .......................... MI2005A1115

(51) Int. Cl.
*C07D 501/57* (2006.01)
*C07D 501/12* (2006.01)
(52) U.S. Cl. ....................................... 540/220; 540/221
(58) Field of Classification Search ................. 540/220, 540/221
See application file for complete search history.

(56) References Cited

U.S. PATENT DOCUMENTS

| 4,263,432 A | | 4/1981 | Iwanami et al. |
| 4,908,443 A | * | 3/1990 | Abe et al. .................... 540/221 |
| 6,583,291 B2 | * | 6/2003 | Zenoni et al. ............... 548/213 |
| 2006/0281915 A1 | * | 12/2006 | Zenoni et al. ............... 540/222 |
| 2007/0093657 A1 | * | 4/2007 | Fogliato et al. ............. 540/220 |

OTHER PUBLICATIONS

Masaru Iwanami, et al., "Synthesis of New Cephamycin Derivatives and a Novel Rearrangement Between Isothiazolethioacetamides and 1,3-Dithietanecarboxamides", Chemical and Pharmaceutical Bulletin, vol. 28, No. 9, XP-002209216, 1980, pp. 2629-2636.

Masaharu Fujimoto, et al., "Process Development and Pilot-scale Synthesis of Cefotetan", Organic Process Research & Development, vol. 8, No. 6, XP-002397340, 2004, pp. 915-919.

* cited by examiner

*Primary Examiner*—Mark L Berch
(74) *Attorney, Agent, or Firm*—Oblon, Spivak, McClelland, Maier & Neustadt, P.C.

(57) ABSTRACT

The invention relates to a method for obtaining cefotetan acid substantially free of tautomer, by treating crude cefotetan with $Al^{3+}$ ions which cause the tautomer to precipitate. The precipitate is eliminated by filtration to provide a solution from which practically tautomer-free cefotetan is obtained.

6 Claims, No Drawings

PROCESS FOR OBTAINING CEFOTETAN WITH HIGH YIELD

BACKGROUND OF THE INVENTION

Field of the Invention and Description of Related Art

U.S. patent application Ser. No. 11/410,022 of the present applicant relates to a process for obtaining cefotetan of formula (I)

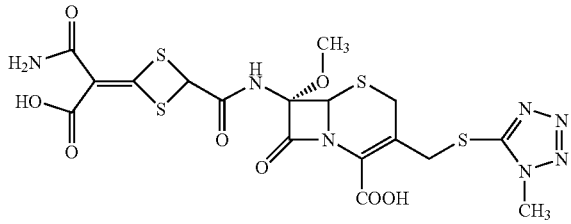

substantially free of the disodium salt tautomer of formula (II)

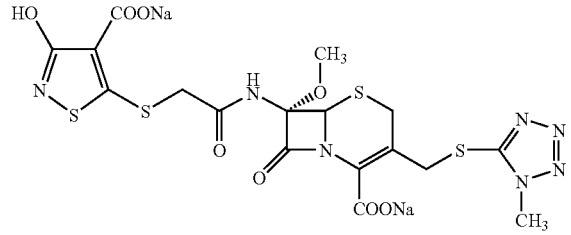

This process makes it possible to obtain a substantially pure cefotetan acid, but has the drawback of being rather lengthy and poorly productive: in other words, it is not particularly suitable for industrial application with the production of large batches.

SUMMARY OF THE INVENTION

The present applicant has therefore sought to devise a simple process which is easy to use and is highly productive. As a result of these efforts, the present inventors have surprisingly found that cefotetan can be recrystallized in pure form, substantially free of tautomer (less than 0.2%), by an easily applied process.

This process is based on the capacity of the cefotetan tautomer to bind to $Al^{3+}$ ions which can be provided in the form of aluminium chloride or as neutral alumina, or even to ions such as $Fe^{3+}$ or $Cr^{3+}$ (probably by forming stable complexes with the oxygen atoms present on the isothiazole part of the molecule of the tautomer of formula (II) at around pH 7.0, to form a precipitate which is eliminated by filtration, while the cefotetan remains in aqueous solution as alkaline carboxylate.

A further advantage of the present method is the ease of recovery of the neutral alumina used in the process, so that it can be recycled with considerable cost saving.

The process of the invention enables cefotetan of formula (I) to be obtained containing up to 0.2% of the tautomer of formula (II) in its acid form and with a K.F. up to 2.5%, concentration on dry basis at least 99.0% and free of solvents, both in the acid form and in the sodium salt obtained from it.

This process is characterised in that an aqueous solution of crude cefotetan cooled to between 0° and +4° C. is brought into contact with $Al^{3+}$ ions originating from a reagent chosen from neutral alumina, anhydrous aluminium trichloride and aluminium trichloride hexahydrate, or with $Fe^{3+}$ or $Cr^{3+}$ ions, to cause formation of a precipitate with the aforesaid tautomer compound, at pH within the range 7.0-7.2, this precipitate being eliminated by filtration to provide a solution containing cefotetan substantially free of tautomer, from which the cefotetan is precipitated by acidification to pH within the range 1.3-1.5 and isolated by filtration between 0° and +4° C. to provide a substantially tautomer-free cefotetan with a K.F. up to 2.5%, concentration on dry basis at least 99.0% and free of solvents.

DETAILED DESCRIPTION OF THE INVENTION

The implementation of the process will be more apparent from the ensuing detailed description of a practical embodiment thereof, given by way of non-limiting example.

EXAMPLE 1

Use of Neutral Alumina 300 g of wet crude cefotetan originating from synthesis and equivalent to about 80 g of pure cefotetan are suspended in 800 ml of osmotized water. The suspension is cooled to between 0° and +4° C., and 35 g of sodium bicarbonate are added in portions, without exceeding pH 6.8.

The pH is corrected to 7.0-7.2 with a solution of 8 g sodium bicarbonate in 100 ml of osmotized water. 120 g of neutral alumina are added, and the pH maintained at 7.1-7.2 between 0° and +4° C. by adding carbon dioxide or an 8% sodium bicarbonate solution. The mixture is agitated for 60 min, the pH is corrected to 6.4 with carbon dioxide, and the alumina is filtered off and washed three times with 100 ml osmotized water.

The pH is corrected to 5.3-5.5 with 5% HCl again at between 0° and +4° C. Agitation is again applied and the cefotetan initially precipitated returns into solution, 1.5 g of decolorizing carbon are added and the mixture agitated at between 0° and +4° C. for 20 min. It is again filtered and the filter washed 3 times with 100 ml of osmotized water.

The pH of the rich aqueous solution is lowered to 1.3-1.5 by adding 15% HCl at between 0° and +40° C. over about 60 min. The mixture is agitated at between 0° and +4° C. for 40 min, and then filtered under vacuum, washing the filter 3 times with 100 ml of osmotized water, acidified with HCl to a content of about 0.1% and cooled to between 0° and +4° C., then washing twice with 100 ml osmotized water alone, pre-cooled to between 0° and +4° C. About 200 g of wet cefotetan are obtained, which is dried under vacuum at 24°-27° C. under a light stream of nitrogen.

Yield: 65-70 g of pure cefotetan, K.F. ≦2.5%, concentration on dry basis ≧99.0%, tautomer ≦0.2%, solvent free.

EXAMPLE 2

Use of Anhydrous Aluminium Trichloride 60.72 g of wet crude cefotetan, at a concentration of 24,7% and containing between 2.5% and 3.0% of tautomer, are fed into 270 ml of demineralized water between 0° and +5° C. After 20 min of agitation, 12.0 g of potassium bicarbonate are added in 15 minutes still at 0° and +5° C. The mixture is stirred for half hour at 0° and +5° C., complete solubilization is obtained and the pH is stabilized at 7.0.

The solution is kept under vacuum at between 0° and +5° C. to remove the dissolved carbon dioxide, the pH rising to 7.3-7.4. Draw-off of carbon dioxide under vacuum is continued while maintaining the pH between 7.3 and 7.4 by adding 1N HCl. After about 30 min the solution appears perfectly clear. At this point 2.0 g of anhydrous $AlCl_3$ are added in small portions of about 0.16 g each, over about half hour while maintaining the temperature between 0° and +5° C. and the pH between 7.3 and 6.6. The additions of anhydrous $AlCl_3$ and aspiration to remove the carbon dioxide are alternated in order to maintain the pH within the range of 6.6 to 7.3. On termination of the anhydrous $AlCl_3$ addition the mixture is maintained under agitation and reduced pressure for 45-50 minutes at between 0° and +5° C., the pH being maintained at 6.9-7.1 by small additions of 1N HCl. The pressure is returned to atmospheric, the pH is fixed at 6.9 and the solution filtered between 0° and +5° C. through a porous septum covered with the following layers starting from the bottom: fabric, cotton, celite filter. The reaction solution, maintained between 0° and +5° C., is filtered under minimum vacuum, checking that the pH remains constant between 6.9 and 7.1. The filtered solution is cloudy and is re-filtered through the same filter a further three times without however obtaining a perfectly clear solution. The filter is finally washed with 4×80 ml portions of cold demineralized water. The pH is corrected to 4.5-4.7 with 15% HCl at between 0° and +5° C. 1.5 g of decolorizing carbon and 0.15 g of EDTA are added. The mixture is filtered and the filter washed with 4×40 ml portions of cold demineralized water. 300 ml of methylethylketone are added followed by 50 g of NaCl. The mixture is agitated for 15 min to completely dissolve the salt, then the pH is lowered to 1.5 with 15% HCl at between 0° and +5° C. The phases are separated after at least 20 min at between 0° and +5° C., then 150 ml of methylethylketone and 50 g of sodium chloride are added to the aqueous phase. When the salt has dissolved, the pH is checked to be ≦1.5, the temperature is raised to 20° C. and the phases allowed to separate for at least 30 min. The two organic phases are pooled, decolorized with 1.5 g of carbon for 15 min, filtered and the filter washed 3 times with 25 ml methylethylketone. The decolorized organic solution is concentrated to 260-280 ml by distilling off the methylethylketone under reduced pressure at 30°-31° C. 320 ml demineralized water are added, the mixture cooled to between 0° and +5° C. and 4.4 g of potassium bicarbonate added under agitation while maintaining the pH between 6.0 and 6.5, and in any event ≦6.5. The phases are separated and the organic phase discarded, while the aqueous phase is corrected to pH 4.5-4.7 with 5% HCl. The aqueous phase is decolorized with 1.0 g carbon at between 0° and +5° C. and maintained under reduced pressure for 20 min. The mixture is filtered, the filter washed twice with 40 ml demineralized water, the system returned to atmospheric pressure and the pH corrected to 3.6-3.7 with 5% HCl at between 0° and +5° C. The temperature is raised to 20° C., the methylethylketone which has remained dissolved is distilled off under reduced pressure, a crystal of pure cefotetan is added and the mixture left to crystallize for 45 min at pH 3.6-3.7, while maintaining reduced pressure to remove further methylethylketone which may be present. Atmospheric pressure is restored and 5% HCl dripped in over 15 min until pH 3.0.

Reduced pressure is again applied and the mixture heated to 30° C., the pH then being lowered to 2.5 with 5% HCl over 15 min. The operation is repeated to reduce the pH firstly to 2.0 and then to 1.5 with 5% HCl, each time returning to reduced pressure at 30° C., until pH 1.5 remains constant for 30 min. The mixture is cooled to between 0° and +5° C. and agitated for 60 min under reduced pressure. Atmospheric pressure is restored, the mixture filtered, the filter washed with 61 ml of 1% HCl at between 0° and +5° C., then with 61 ml of demineralized water at the same temperature.

On drying, 11.0 g of cefotetan are obtained with a concentration on dry basis ≧99.0% and with tautomer ≦0.2%, K.F. <2.5%.

The same results are obtained on using aluminium trichloride hexahydrate in a quantity equivalent to the anhydrous aluminium trichloride of the aforedescribed example.

EXAMPLE 3

Recovery of Spent Alumina

To recover the spent neutral alumina the wet neutral alumina originating from 240 kg of virgin neutral alumina is loaded into a comber filter. A solution of 40 kg of 30% soda in 1000 l of demineralized water is eluted at ≦20° C. Nitrogen is blown into the filter for drying purposes and elution is repeated with a further 40 kg of 30% sodium hydroxide in 1000 l demineralized water. When the last fraction is colourless, elution is carried out with at least 10000 l of demineralized water to a pH between 8 and 9.

The regenerated alumina is suspended in 1000 l of demineralized water at a temperature of ≦20° C. Agitation is applied and the pH corrected to 6.7-7.3 with 5% HCl until constant pH within this range. The mixture is filtered, and washed with at least 1000 l of demineralized water in portions, until the last wash presents a conductivity <500 microSiemens (μS).

310-320 kg of wet product are recovered, corresponding to 220-230 kg of dry neutral alumina.

What is claimed is:
1. A process for obtaining cefotetan of formula (I)

(I)

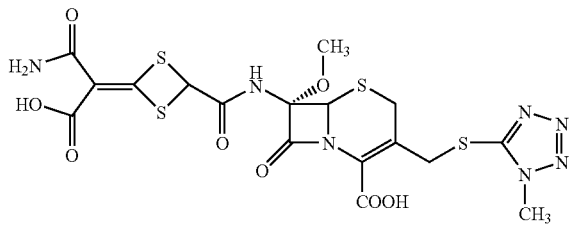

containing not more than 0.2% of the acid form of the tautomer of formula (II) wherein H appears in place of Na (II)

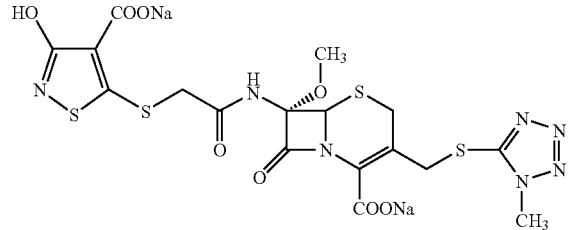

wherein the cefotetan has a K.F up to 2.5%, and a purity on dry basis at least 99.0%,
wherein an aqueous solution of crude cefotetan cooled to between 0° and +4° C. is brought into contact with $Al^{3+}$ ions originating from a reagent chosen from the group consisting of neutral alumina, anhydrous aluminium trichloride and aluminium trichloride hexahydrate, or with $Fe^{3+}$ or $Cr^{3+}$ ions, to cause formation of a precipitate with the aforesaid tautomer compound, at pH within the range 7.0-7.2, this precipitate being eliminated by filtration to provide a solution containing cefotetan of high purity, from which the cefotetan is precipitated by acidification at pH within the range 1.3-1.5 and isolated by filtration between 0° and +4° C. to provide a cefotetan with a K.F. up to 2.5%, and having a purity on a dry basis of at least 99.0%.

2. A process, comprising:

contacting an aqueous solution comprising at least one of a compound of formula (I) and a carboxylate salt thereof, and at least one of a compound of formula (II) and a compound of formula (II) in which H appears in place of the Na atoms, with one or more of $Al^{3+}$ ions from neutral alumina, $Al^{3+}$ ions from anhydrous aluminum trichioride, $Al^{3+}$ ions from aluminum trichioride hexahydrate, $Fe^{3+}$ ions and $Cr^{3+}$ ions at a temperature of between 0 and +4°; and

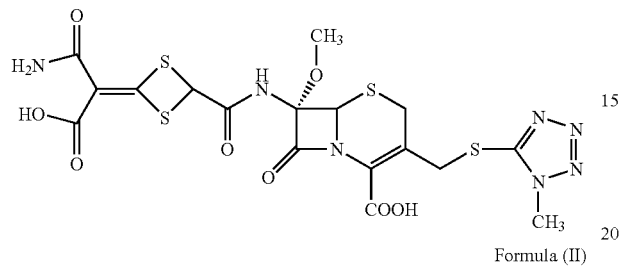

Formula (I)

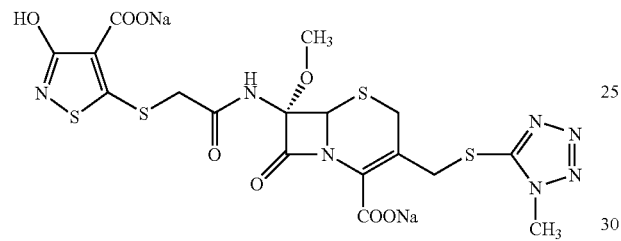

Formula (II)

adjusting the pH of the aqueous solution to 7.0-7.2 to precipitate a salt or a complex of the compound of formula (II) to form a supernatant solution comprising at least one of a compound of formula (I) and a carboxylate salt thereof.

3. The process according to claim 2, further comprising:

after the salt or the complex of the compound of formula (II) is precipitated, filtering the supernatant solution to separate the compound of formula (I) or a carboxylate thereof from the precipitated salt or the precipitate complex of the compound of formula (II) and to form a first filtered solution.

4. The process according to claim 3, further comprising:

adjusting the pH of the first filtered solution to from 1.3 to 1.5 to precipitate the compound of formula (I).

5. The process according to claim 4, further comprising:

isolating the compound of formula (I) by filtering the first filtered solution having a pH of from 1.3 to 1.5, and drying to form a cefotetan having a K.F. of up to 2.5% that is at least 99.0% pure on a dry basis.

6. The process according to claim 1, wherein the aqueous solution comprising the compound of formula (I) and the compound of formula (II) is contacted with one or more of $Al^{3+}$ ions from neutral alumina, $Al^{3+}$ ions from anhydrous aluminum trichloride, and $Al^{3+}$ ions from aluminum trichloride hexahydrate.

* * * * *